(12) United States Patent
Patterson

(10) Patent No.: US 10,987,240 B2
(45) Date of Patent: Apr. 27, 2021

(54) HAND POSITIONING SYSTEMS

(71) Applicant: Ann Marie Patterson, Calgary (CA)

(72) Inventor: Ann Marie Patterson, Calgary (CA)

( * ) Notice: Subject to any disclaimer, the term of this patent is extended or adjusted under 35 U.S.C. 154(b) by 566 days.

(21) Appl. No.: 15/994,685

(22) Filed: May 31, 2018

(65) Prior Publication Data

US 2019/0365556 A1   Dec. 5, 2019

(51) Int. Cl.
*A61G 15/00* (2006.01)
*A61F 5/01* (2006.01)
*A61F 5/10* (2006.01)

(52) U.S. Cl.
CPC ............... *A61F 5/0118* (2013.01); *A61F 5/10* (2013.01)

(58) Field of Classification Search
CPC ...... A61F 13/104; A61F 13/10; A61F 5/0118; A61F 5/0104; A61F 5/0102; A61F 5/013; A61F 5/05866; A61F 5/05875; A61F 5/10; A61F 5/30; A61F 5/32; A61F 5/058; A61F 5/37; A61F 5/019; A61F 5/3761; A61F 5/3769; A61F 5/3776; A61F 5/3792; A61F 5/3715; A61F 5/3723; A61G 13/12; A61G 13/1205; A61G 13/124; A61G 13/1235; A61G 13/0045; A61G 7/075; A63B 23/16; A63B 21/028; A63B 21/026; A63B 21/0601; A63B 21/0607; A63B 21/4035; A61H 2205/065; A47G 2200/04; A47G 2200/046; Y10T 24/39; A45C 13/30; A45C 2013/303; B65D 63/18

USPC .......... 602/21; 128/845, 878, 879, 880, 877, 128/869; 482/44; 5/646, 647; 16/114.1, 16/411, 428, 430
See application file for complete search history.

(56) References Cited

U.S. PATENT DOCUMENTS

| | | | |
|---|---|---|---|
| 3,581,740 A | 6/1971 | Sherbourne | |
| 3,703,894 A | 11/1972 | Galloway et al. | |
| 4,558,694 A | 12/1985 | Barber | |
| 4,977,621 A | 12/1990 | Robert | |
| 4,977,890 A | 12/1990 | Mann | |
| 5,020,515 A | 6/1991 | Mann et al. | |
| 5,766,142 A | 6/1998 | Hess | |
| 6,618,624 B2 | 9/2003 | Elias | |
| 6,694,523 B2 | 2/2004 | Hurst | |
| 8,209,771 B1 | 7/2012 | Sykes | |
| 2017/0100638 A1* | 4/2017 | Breibart | ............. A63B 21/4013 |

FOREIGN PATENT DOCUMENTS

DE    102004041237    3/2006

* cited by examiner

*Primary Examiner* — Victoria J Hicks
(74) *Attorney, Agent, or Firm* — Runyan Law; Charles Runyan

(57) ABSTRACT

An apparatus for positioning a human hand; the apparatus is designed to assist stroke victims or individuals with no or limited use of their hands. It allows for better airflow to the palm and fingers, keeps hands dry, and reduces collection of dirt, oil, odor-causing germs, etc. from collecting in the palm region. The device may consist of two cylindrical tubes secured together with bands and to the hand with a simple-to-adjust strap.

20 Claims, 5 Drawing Sheets

HAND POSITIONING SYSTEMS

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

1. Field of the Invention

The present invention relates generally to the field of orthopedic devices and more specifically relates to orthopedic devices specially adapted for supporting and positioning the hand.

2. Description of Related Art

Patients who have impaired hand function due to a stroke or other conditions often struggle to maintain cleanliness of their hands, particularly in the region of the palm. Individuals with severe hand impairment cannot grip a tissue or towel and keep it in place to prevent hands from sweating or from collecting dirt, which can harbor odor-causing bacterial growth. It is very embarrassing for a stroke victim to have dirty hands or hands with an off-putting odor when a visitor or loved one attempts to hold their hand. A low cost and easy-to-use apparatus that overcomes the above-noted problems would benefit many.

Medical splints for immobilizing the hand have been attempted in the past. For example, U.S. Pat. No. 4,558,694 to Barber relates to an ulnar deviation splint. The described ulnar deviation splint includes a hand splint which is designed to support the metacarpophalangeal joints and resist ulnar drift of the proximal phalanges, while at the same time avoiding restriction of normal hand use. The splint has a bendable support frame of a generally oblong shape which is adapted to fit the palmar arch of the hand. Four generally rounded finger separators are attached to the frame to separate each of the fingers and provide lateral resistance to ulnar drift thereof. Preferably the support frame and finger separators are formed of wire. The entire splint is enclosed in a pliant foamed cushioning material which according to one embodiment can be further covered with an abrasion resistant, flexible outer sheeting material to resist wear. Straps or other fastening means are used to secure the splint against the hand. A process for making the splint is also provided. Unfortunately, such splint devices are incapable of addressing the problems associated with hygiene of the hand noted above.

BRIEF SUMMARY OF THE INVENTION

In view of the foregoing disadvantages inherent in the known orthopedic devices art, the present disclosure provides a novel hand positioning system. The general purpose of the present disclosure, which will be described subsequently in greater detail, is to assist in positioning the hand of an individual having impaired hand function to allow for better airflow to the palm and fingers. The device functions to keep the hands dry, reduces collection of dirt, oils, and other materials supporting bacterial growth. In addition, the device is capable of improving flexibility of the hand by moving the fingers away from the palm.

An apparatus for positioning a human hand is disclosed herein. The apparatus includes a first resilient bar member adapted to extend across a palm region of the human hand; a second resilient bar member adapted to extend across the palm region of the human hand, the second resilient bar member generally parallel to the first resilient bar member; at least one binder adapted to bind the first resilient bar member to the second resilient bar member; and an adjustable retaining member adapted to adjustably retain the first resilient bar member and the second resilient bar member adjacent the palm region, the adjustable retaining member may include a first retaining end, a second retaining end, and a hand-encircling portion extending between the first retaining end and the second retaining end; the first retaining end and the second retaining end configured to extend between and be retained by the first resilient bar member and the second resilient bar member; and the hand-encircling portion configured to form a retaining loop extending from between the first resilient bar member and the second resilient bar member and extending across a back portion of the human hand.

A method of using the apparatus is also disclosed herein. The method may comprise the steps of: providing the above-described apparatus for positioning a human hand; positioning the first resilient bar member and the second resilient bar member adjacent the palm region of the human hand; and retaining the first resilient bar member and the second resilient bar member adjacent the palm region of the human hand by encircling a portion of the human hand with the adjustable retaining member.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a hand positioning system, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to orthopedic devices and more particularly to a hand positioning system as used to improve the orthopedic devices specially adapted for supporting and positioning the hand.

Generally, the device of the present disclosure is placed in the palm of a hand and easily secured with straps to maintain the palm in an open condition, thus assisting in preventing odor-causing dirt, grease, and grime from collecting on the palm. The device may consist of two one-inch diameter tubes secured together with bands and to the hand with a simple-to-adjust strap. It allows for better airflow to the palm and fingers, keeps hands dry, and reduces the collection of dirt, oil, smells, germs, etc. within the palm. It also allows for improved flexibility, muscle memory and hand/finger muscle maintenance. Patients will appreciate the ease of use and the fact that the device is effective in keeping a user's hands fresh, easy to clean, and less likely to smell. The device is formed from an easy to clean and hypoallergenic foam or foam-related spacer. It allows for increased air flow, is simple to use and clean. It also offers resistance for users with because the palm is open, and users can flex against it in a more comfortable position. Moreover, the device provides resistance for users who have no or limited use of their hands. It has been observed that after the device has been used for an hour or so the palm tends to stay open for an extended period of time before slowing closing again, thus the beneficial effect is prolonged well after use.

Figure 1:
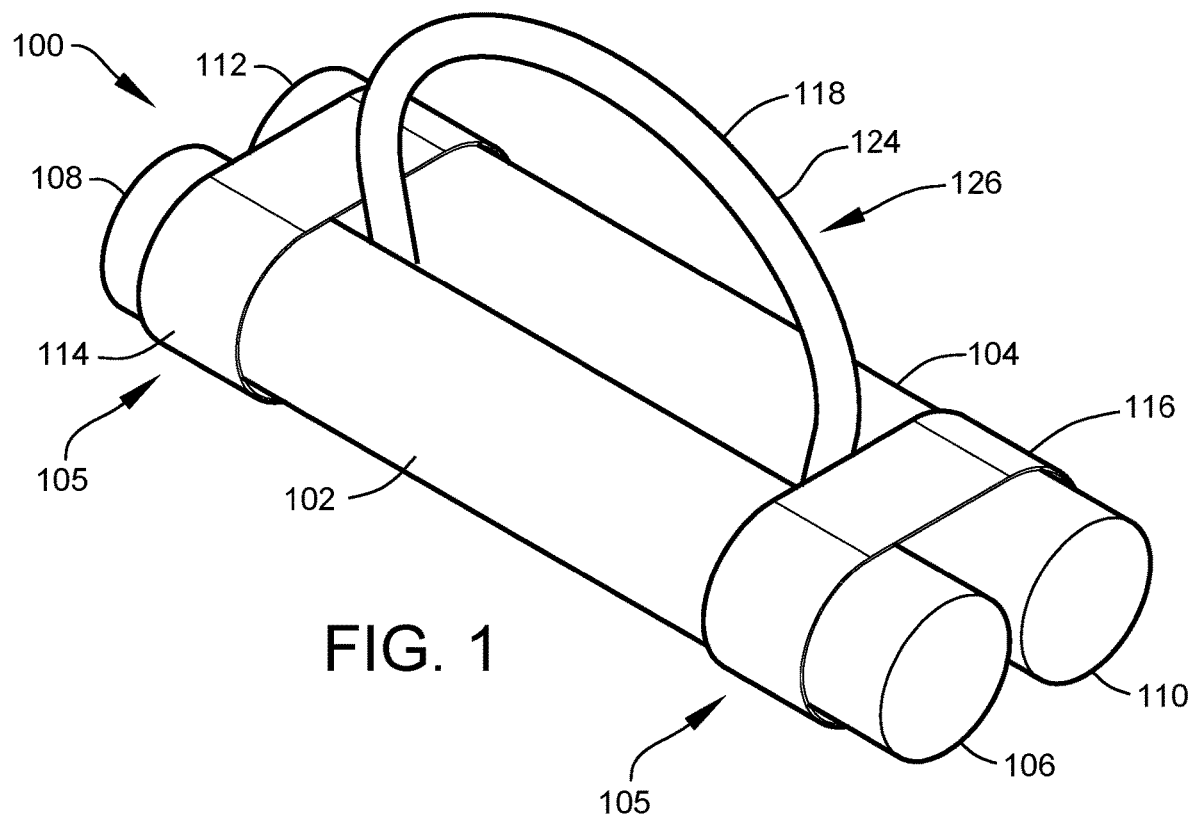
FIG. 1 is a front perspective view of the apparatus for positioning a human hand, according to an embodiment of the disclosure.
Figure 2:
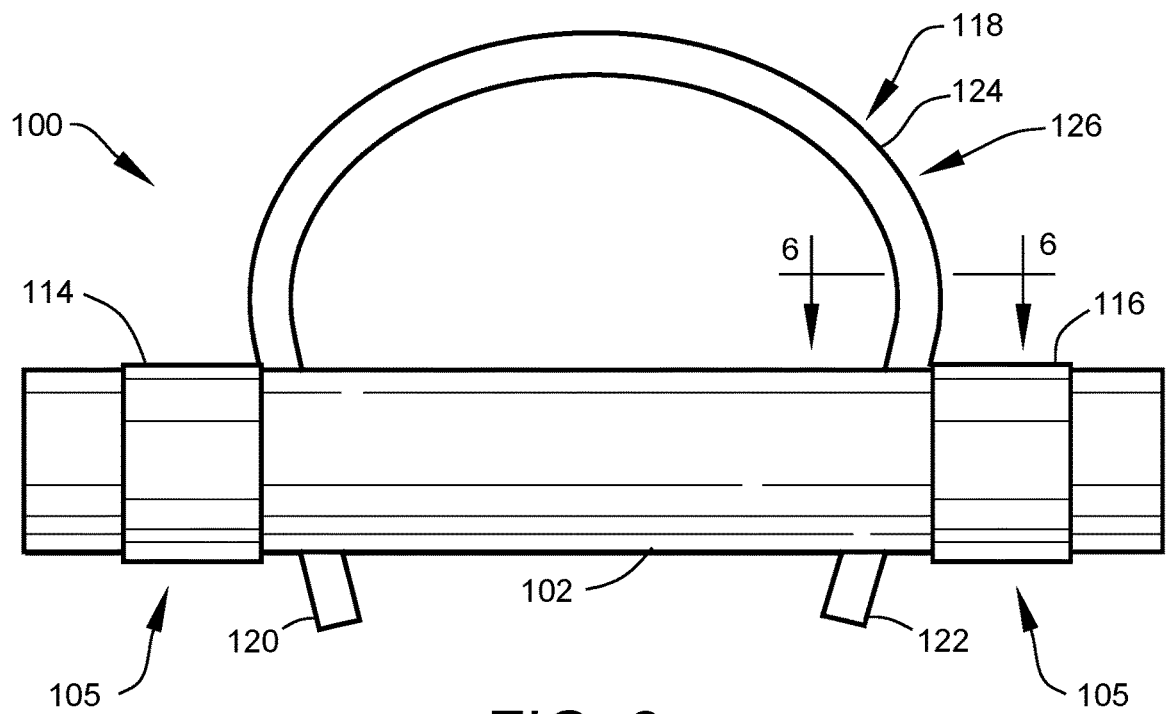
FIG. 2 is a front view of the apparatus of FIG. 1, according to an embodiment of the present disclosure.
Figure 3:
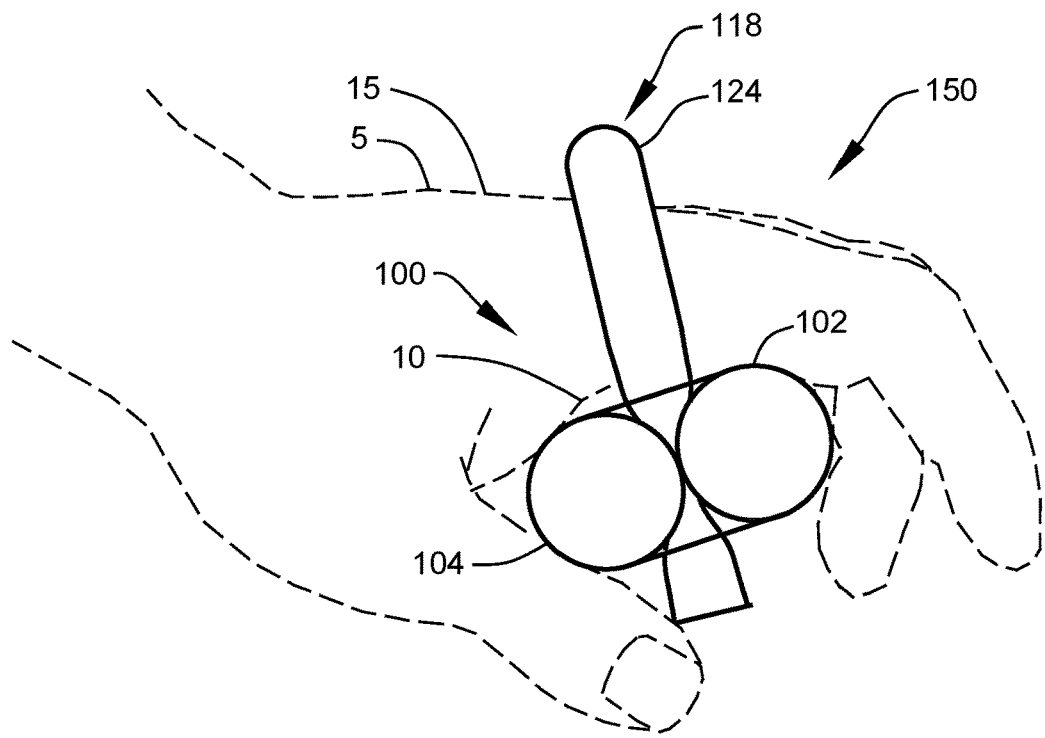
FIG. 3 is an end view of the apparatus of FIG. 1, during an 'in-use' condition, according to an embodiment of the present disclosure.

Referring now more specifically to the drawings by numerals of reference, there is shown in FIGS. 1-7, various views of an apparatus 100 for positioning a human hand 5. FIG. 1 shows the apparatus 100, according to an embodiment of the present disclosure. FIG. 2 is a front view of the apparatus 100 of FIG. 1. FIG. 3 is an end view of the apparatus 100 of FIG. 1, during an 'in-use' condition 150, according to an embodiment of the present disclosure. As illustrated, the apparatus 100 may include a first resilient bar member 102 and a second resilient bar member 104. The second resilient bar member 104 may be located in contact with and generally parallel to the first resilient bar member 102, as shown. Both the first resilient bar member 102 and the second resilient bar member 104 may be adapted to extend across a palm region 10 of a human hand 5, as shown. At least one binder 105 is adapted to bind the first resilient bar member 102 to the second resilient bar member 104. In the depicted embodiment of the disclosure, multiple binders 105 are provided, as shown.

An adjustable retaining member 118 is provided to adjustably retain the first resilient bar member 102 and the second resilient bar member 104 in a position adjacent to the palm region 10. The adjustable retaining member 118 may include a first retaining end 120, a second retaining end 122, and a hand-encircling portion 124 extending between the first retaining end 120 and the second retaining end 122, as shown. The first retaining end 120 and the second retaining end 122 may be configured to extend between and be retained by the first resilient bar member 102 and the second resilient bar member 104, as shown in FIG. 1. The hand-encircling portion 124 may be configured to form a retaining loop 126 extending from between the first resilient bar member 102 and the second resilient bar member 104 and extending across the back portion 15 of the human hand 5, as shown.

Figure 4:
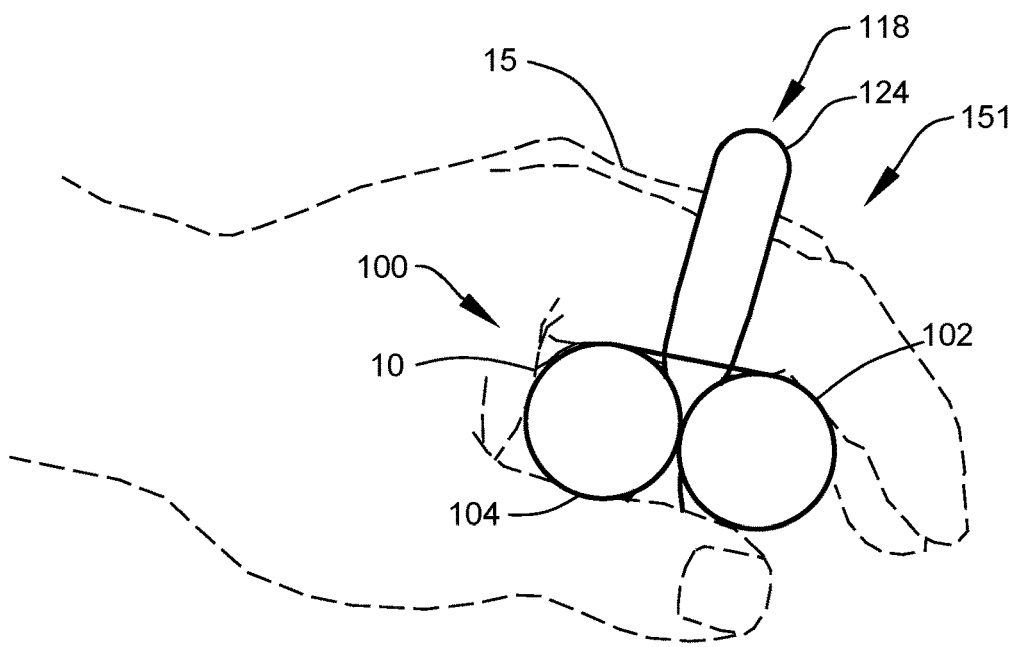
FIG. 4 is an end view of the apparatus of FIG. 1, during an alternate 'in-use' condition, according to an embodiment of the present disclosure.

FIG. 4 is an end view of the apparatus 100 of FIG. 1, during an alternate 'in-use' condition 151, according to an embodiment of the present disclosure. The adjustable retaining member 118 is designed to allow for alternate placements of the member over the back of the hand 5, as best suited the shape of the hand and comfort of the user. For example, FIG. 3 shows the adjustable retaining member 118 extending over the top of the hand between the wrist and knuckles while FIG. 4 shows the adjustable retaining member 118 extending in an alternate position over the fingers.

Figure 5:
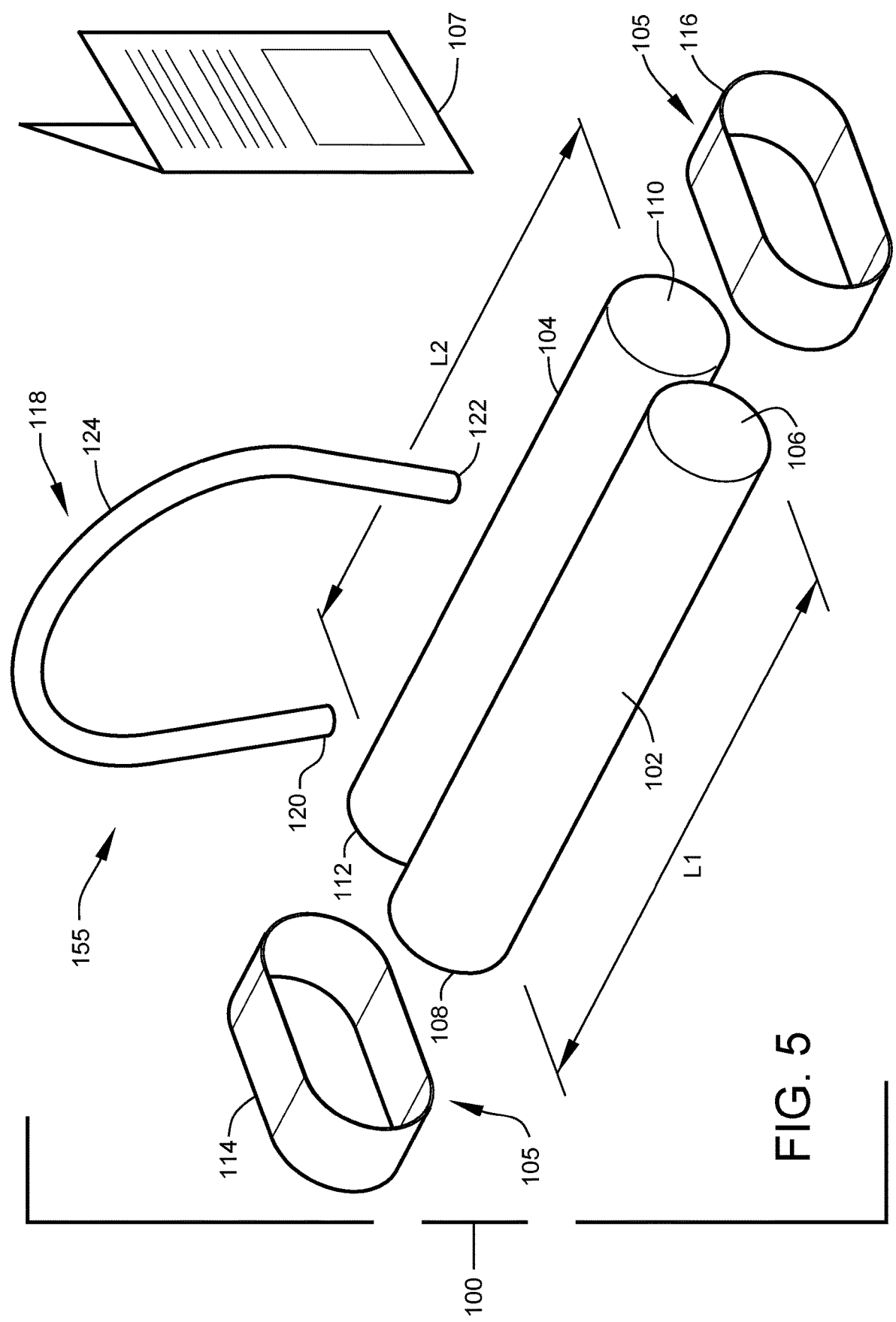
FIG. 5 is an exploded view of the apparatus of FIG. 1, according to an embodiment of the present disclosure.

FIG. 5 is an exploded view of the apparatus 100 of FIG. 1, according to an embodiment of the present disclosure. As illustrated, the first resilient bar member 102 has a first right end 106, a first left end 108 opposite the first right end 106, and a first bar length L1 extending between the first right end 106 and the first left end 108. The second resilient bar member 104 has a second right end 110, a second left end 112 opposite the second right end 110, and a second bar length L2 extending between the second right end 110, and the second left end 112. In one embodiment of the disclosure, the first bar length L1 and the second bar length L2 are substantially equal, as shown.

In one embodiment of the disclosure, a first binding band 114 and a second binding band 116 are provided to encircle the first resilient bar member 102 and the second resilient bar member 104, as shown. The first binding band 114 may be located near (proximate) the first left end 108 of the first resilient bar member 102 and the second left end 112 of the second resilient bar member, as shown. The second binding band 116 may be located proximate the first right end 106 of the first resilient bar member 102 and the second right end 110 of the second resilient bar member 104, as shown.

The first resilient bar member 102 and the second resilient bar member 104 may each have a circular cross-sectional shape and a uniform diameter of about one inch. Upon reading this specification, it should be appreciated that, under appropriate circumstances, considering such issues as user preferences, design preference, structural requirements, marketing preferences, cost, available materials, technological advances, etc., other physical arrangements such as, for example, larger or smaller diameters, alternate cross-sectional shapes, ergonomic shapes, custom profiles designed to fit the hand of specific user, etc., may be sufficient.

The adjustable retaining member 118 may also have a circular cross-sectional shape and may have a uniform diameter of between about one quarter and about one-half inch. The adjustable retaining member 118 may have a length of between about three inches and about ten inches, when measured end-to-end. Upon reading this specification, it should be appreciated that, under appropriate circumstances, considering such issues as user preferences, design preference, structural requirements, marketing preferences, cost, available materials, technological advances, etc., other physical arrangements such as, for example, longer or shorter lengths, larger or smaller diameters, the use of alternate bands, etc., may be sufficient.

The first resilient bar member 102, the second resilient bar member 104, and the adjustable retaining member 118 may each be constructed from at least one resilient material, more preferably, a hypoallergenic resilient material, more preferably, hypoallergenic, resilient, and non-moisture absorbent material. Most preferably, first resilient bar member 102, the second resilient bar member 104, and the adjustable retaining member 118 may each be constructed from at least one closed-cell foam. In one embodiment of the present disclosure, the above-noted parts of apparatus 100 are constructed from closed-cell polyethylene foam. Polyethylene foam was selected for its light weight and durability. In addition, closed-cell polyethylene foam was found to provide each of the above-noted performance characteristics. Moreover, closed-cell polyethylene foam allows the first resilient bar member 102, the second resilient bar member 104, and the adjustable retaining member 118 to be produced by an efficient and lower-cost extrusion process. Colorants and additive may be blended with the thermoplastic raw materials forming the polyethylene foam to create a selected density, structure, and color, and to add beneficial characteristics like flame resistance and UV-stability, etc. Those with ordinary skill in the art will now appreciate that upon reading this specification and by their understanding the art of polymer chemistry as described herein, methods of formulating and forming such polymer-based materials will be understood by those knowledgeable in such art. Upon reading this specification, it should be appreciated that, under appropriate circumstances, considering such issues as user preferences, design preference, structural requirements, marketing preferences, cost, available materials, technological advances, etc., other material arrangements such as, for example, the use of alternate polymers, the use of molded pieces, adding antibacterial coatings or admixtures, etc., may be sufficient.

Figure 6:
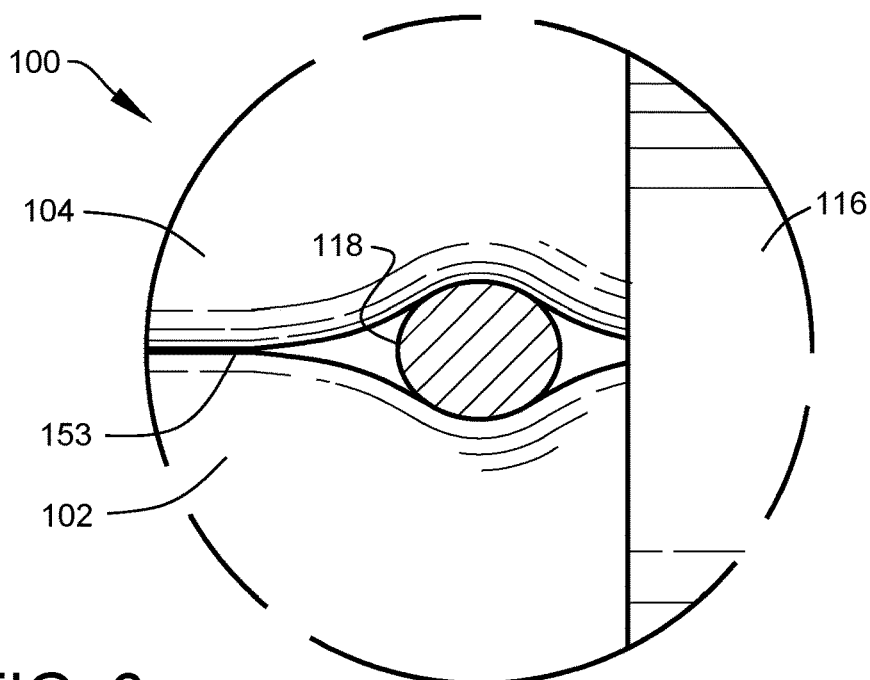
FIG. 6 is a sectional view through the section 6-6 of FIG. 2, according to an embodiment of the present disclosure.
Figure 7:
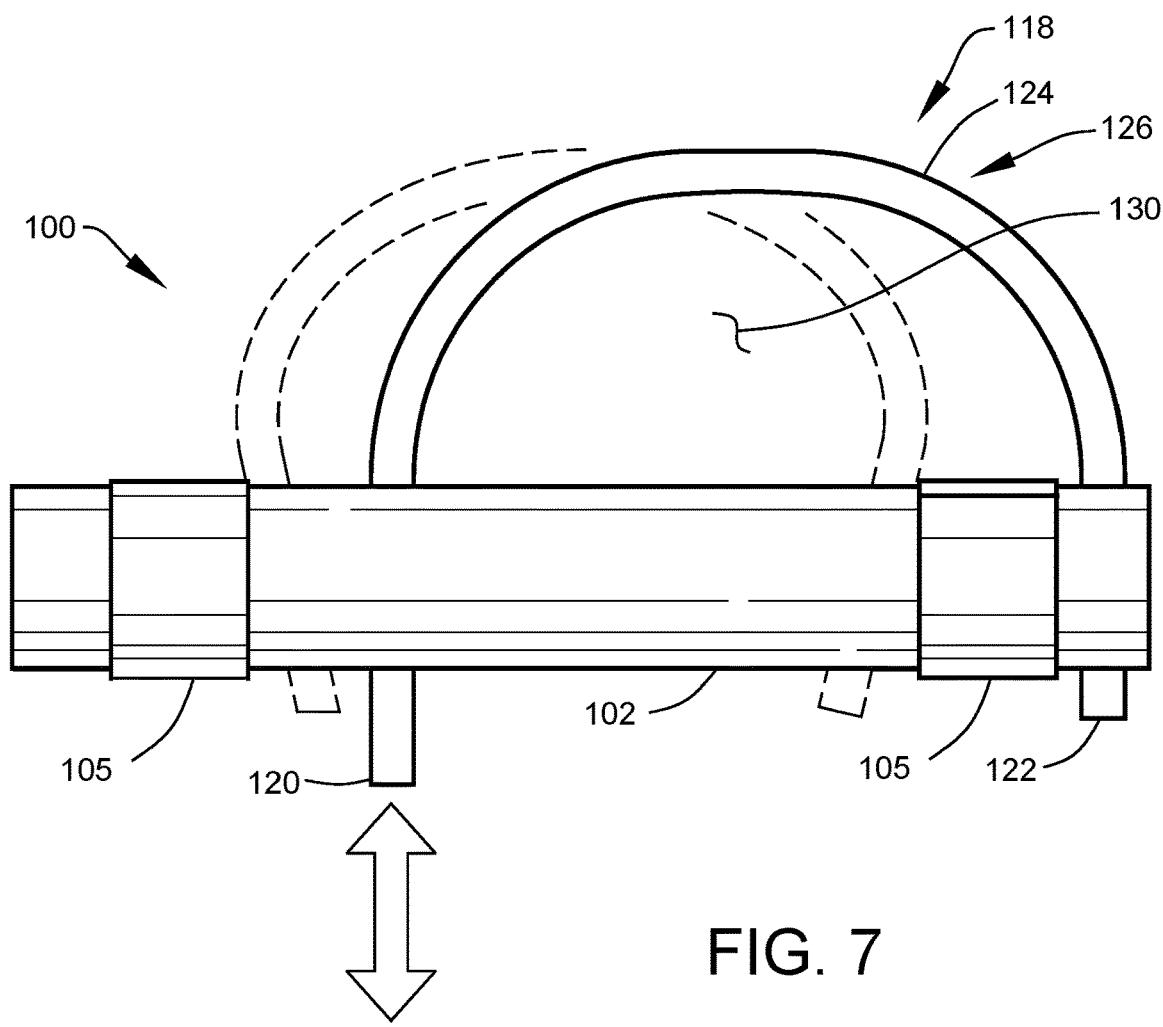
FIG. 7 is a front view of the apparatus of FIG. 1, illustrating the positioning of an adjustable retaining member, according to an embodiment of the present disclosure.

FIG. 6 is a sectional view through the section 6-6 of FIG. 2, according to an embodiment of the present disclosure. FIG. 7 is a front view of the apparatus 100 of FIG. 1, illustrating the positioning of an adjustable retaining member, according to an embodiment of the present disclosure. The first retaining end 120 and the second retaining end 122 of the adjustable retaining member 118 are each movably retained between the first resilient bar member 102 and the second resilient bar member 104 by frictional engagement, as shown in the section view of FIG. 6. Referring to FIG. 7, the retaining loop 126 has a loop opening 130 and the size of the loop opening 130 is adjustable by altering a position of the first retaining end 120 or the second retaining end 122, or a combination of both, relative to the first resilient bar member 102 and the second resilient bar member 104. More specifically, the size of the retaining loop 126 may be adjusted by pushing or pulling the ends of the adjustable retaining member 118 through the narrow gap 153 formed between the first and second resilient bar members.

Because the adjustable retaining member 118 is not rigidly fixed to the first and second resilient bar members, the position of engagement of the adjustable retaining member 118 may be changed to best fit the hand of the user. FIG. 7 shows the second retaining end 122 moved to the opposite side of the second binding band 116.

The apparatus 100 may also be arranged as a kit 155 (see FIG. 5). In particular, the pet transport apparatus 100 may further include a set of instructions 107. The instructions 107 may detail functional relationships in relation to the structure of the apparatus 100 such that the apparatus 100 can be used, maintained, or the like, in a preferred manner.

Figure 8:
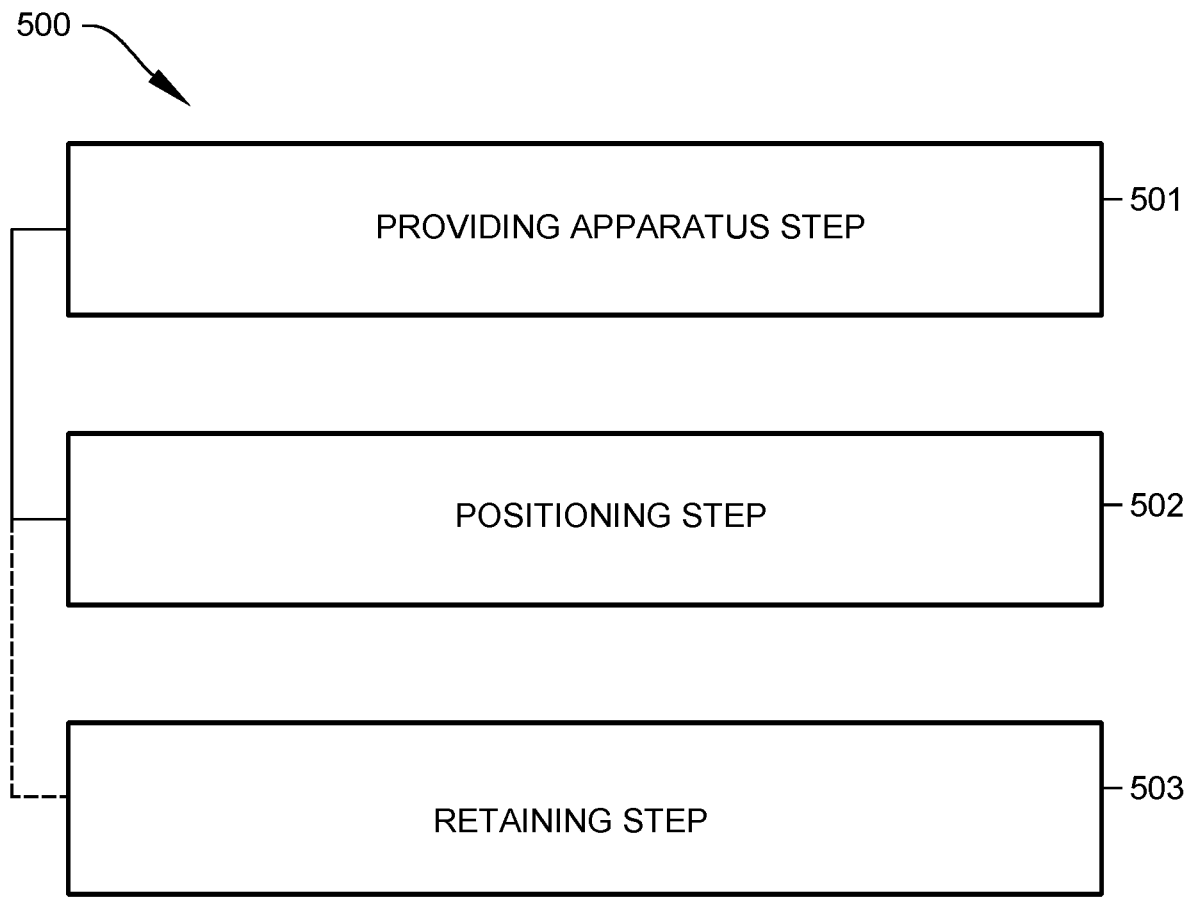
FIG. 8 is a flow diagram illustrating a method of use for apparatus for positioning a human hand, according to an embodiment of the present disclosure.

FIG. 8 is a flow diagram illustrating a method 500 relating to the positioning a human hand, according to an embodiment of the present disclosure. As illustrated, the a method 500 may include the steps of: step one, 501, providing the apparatus of FIG. 1; step two, 502, positioning the first resilient bar member 102 and the second resilient bar member 104 adjacent the palm region 10 of the human hand 5; and step three, 503, retaining the first resilient bar member 102 and the second resilient bar member 104 adjacent the palm region 10 of the human hand 5 by encircling a portion of the human hand 5 with the adjustable retaining member 118.

It should be noted that step 503 is an optional step and may not be implemented in all cases. Optional steps of method 500 are illustrated using dotted lines in FIG. 8 so as to distinguish them from the other steps of method 500. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for apparatus for positioning a human hand (e.g., different step orders within above-mentioned list, elimination or addition of certain steps, including or excluding certain maintenance steps, etc.), are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. An apparatus for positioning a human hand comprising:
   a first resilient bar member adapted to extend across a palm region of the human hand;
   a second resilient bar member adapted to extend across the palm region of the human hand, the second resilient bar member generally parallel to the first resilient bar member;
   at least one binder adapted to bind the first resilient bar member to the second resilient bar member; and
   an adjustable retaining member adapted to adjustably retain the first resilient bar member and the second resilient bar member adjacent the palm region, the adjustable retaining member including
      a first retaining end,
      a second retaining end, and
      a hand-encircling portion extending between the first retaining end and the second retaining end;
   the first retaining end and the second retaining end configured to extend between and be retained by the first resilient bar member and the second resilient bar member; and
   the hand-encircling portion configured to form a retaining loop extending from between the first resilient bar member and the second resilient bar member and configured to extend across the back portion of the human hand.

2. The apparatus of claim 1, wherein
the first resilient bar member comprises a first right end, a first left end opposite the first right end, and a first bar length extending between the first right end and the first left end; and
the second resilient bar member comprises a second right end, a second left end opposite the second right end, and a second bar length extending between the second right end, and the second left end; and
the first bar length and the second bar length are substantially equal.

3. The apparatus of claim 2, wherein the at least one binder includes
a first binding band configured to encircle the first resilient bar member and the second resilient bar member; and
a second binding band configured to encircle the first resilient bar member and the second resilient bar member.

4. The apparatus of claim 3, wherein
the first binding band is located proximate the first left end of the first resilient bar member and the second left end of the second resilient bar member; and
the second binding band is located proximate the first right end of the first resilient bar member and the second right end of the second resilient bar member.

5. The apparatus of claim 1, wherein the first resilient bar member and the second resilient bar member each have a circular cross-sectional shape.

6. The apparatus of claim 5, wherein the first resilient bar member has a uniform diameter of one inch.

7. The apparatus of claim 5, wherein the second resilient bar member has a uniform diameter of one inch.

8. The apparatus of claim 1, wherein
the first retaining end of the adjustable retaining member is movably retained between the first resilient bar member and the second resilient bar member by frictional engagement; and
second retaining end of the adjustable retaining member is movably retained between the first resilient bar member and the second resilient bar member by frictional engagement.

9. The apparatus of claim 8, wherein a size of the retaining loop is adjustable to fit the human hand by altering a position of at least one of the first retaining end and the second retaining end relative to the first resilient bar member and the second resilient bar member.

10. The apparatus of claim 1, wherein the adjustable retaining member has a circular cross-sectional shape.

11. The apparatus of claim 10, wherein the adjustable retaining member has a uniform diameter of between one quarter and one-half inch.

12. The apparatus of claim 1, wherein the adjustable retaining member is constructed of at least one flexible resilient material.

13. The apparatus of claim 1, wherein the adjustable retaining member has a length of between three inches and ten inches.

14. The apparatus of claim 1, wherein adjustable retaining member is constructed from at least one closed-cell foam.

15. The apparatus of claim 1, wherein the first resilient bar member and the second resilient bar member are constructed from at least one closed-cell foam.

16. The apparatus of claim 1, wherein the first resilient bar member, the second resilient bar member, and the adjustable retaining member are constructed from at least one extruded closed-cell polyethylene foam.

17. An apparatus for positioning a human hand comprising:
a first resilient bar member adapted to extend across a palm region of the human hand;
a second resilient bar member adapted to extend across the palm region of the human hand, the second resilient bar member generally parallel to the first resilient bar member;
at least one binder adapted to bind the first resilient bar member to the second resilient bar member; and
an adjustable retaining member adapted to adjustably retain the first resilient bar member and the second resilient bar member adjacent the palm region, the adjustable retaining member including
a first retaining end,
a second retaining end, and
a hand-encircling portion extending between the first retaining end and the second retaining end;
the first retaining end and the second retaining end configured to extend between and be retained by the first resilient bar member and the second resilient bar member; and
the hand-encircling portion configured to form a retaining loop extending from between the first resilient bar member and the second resilient bar member and configured to extend across the back portion of the human hand;
wherein the first resilient bar member comprises a first right end, a first left end opposite the first right end, and a first bar length extending between the first right end and the first left end;
wherein the second resilient bar member comprises a second right end, a second left end opposite the second right end, and a second bar length extending between the second right end, and the second left end;
wherein the first bar length and the second bar length are substantially equal;
wherein the at least one binder includes
a first binding band configured to encircle the first resilient bar member and the second resilient bar member, and
a second binding band configured to encircle the first resilient bar member and the second resilient bar member;
wherein the first binding band is located proximate the first left end of the first resilient bar member and the second left end of the second resilient bar member;
wherein the second binding band is located proximate the first right end of the first resilient bar member and the second right end of the second resilient bar member;
wherein the first resilient bar member and the second resilient bar member each have a circular cross-sectional shape and a uniform diameter of about one inch;
wherein the first retaining end and the second retaining end of the adjustable retaining member are each movably retained between the first resilient bar member and the second resilient bar member by frictional engagement;
wherein the retaining loop has a loop opening and a size of the loop opening is adjustable by altering a position of at least one of the first retaining end and the second retaining end relative to the first resilient bar member and the second resilient bar member;

wherein the adjustable retaining member has a circular cross-sectional shape and a uniform diameter of between about one quarter and about one-half inch;

wherein the adjustable retaining member has a length of between about three inches and about ten inches; and wherein the first resilient bar member, the second resilient bar member, and the adjustable retaining member are constructed from at least one closed-cell foam.

18. The apparatus of claim 17, further comprising set of instructions; and wherein the apparatus is arranged as a kit.

19. A method of positioning a human hand, the method comprising the steps of:

providing an apparatus for positioning a human hand comprising:

a first resilient bar member adapted to extend across a palm region of the human hand;

a second resilient bar member adapted to extend across the palm region of the human hand, the second resilient bar member generally parallel to the first resilient bar member;

at least one binder adapted to bind the first resilient bar member to the second resilient bar member; and an adjustable retaining member adapted to adjustably retain the first resilient bar member and the second resilient bar member adjacent the palm region, the adjustable retaining member including a first retaining end, a second retaining end, and a hand-encircling portion extending between the first retaining end and the second retaining end;

the first retaining end and the second retaining end configured to extend between and be retained by the first resilient bar member and the second resilient bar member;

and the hand-encircling portion configured to form a retaining loop extending from between the first resilient bar member and the second resilient bar member and configured to extend across the back portion of the human hand;

wherein the first retaining end of the adjustable retaining member is movably retained between the first resilient bar member and the second resilient bar member by frictional engagement; and second retaining end of the adjustable retaining member is movably retained between the first resilient bar member and the second resilient bar member by frictional engagement;

wherein a size of the retaining loop is adjustable to fit the human hand by altering a position of at least one of the first retaining end and the second retaining end relative to the first resilient bar member and the second resilient bar member;

positioning the first resilient bar member and the second resilient bar member adjacent the palm region of the human hand; and retaining the first resilient bar member and the second resilient bar member adjacent the palm region of the human hand by encircling a portion of the human hand with the adjustable retaining member.

20. The method of claim 19, further comprising the step of sizing the retaining loop of the adjustable retaining member to fit the human hand by altering the position of at least one of the first retaining end and the second retaining end relative to the first resilient bar member and the second resilient bar member.

\* \* \* \* \*